(12) United States Patent
Cornil

(10) Patent No.: US 8,997,752 B2
(45) Date of Patent: Apr. 7, 2015

(54) SKIN WOUND TREATMENT METHOD, DRESSING AND BIOCHEMICAL ACTIVATION DEVICE FOR THE USE OF SUCH A METHOD

(71) Applicant: Vivatech Company, Paris (FR)

(72) Inventor: Alain Cornil, Aix-en-Provence (FR)

(73) Assignee: Vivatech Company, Paris (FR)

( * ) Notice: Subject to any disclaimer, the term of this patent is extended or adjusted under 35 U.S.C. 154(b) by 0 days.

(21) Appl. No.: 13/870,089

(22) Filed: Apr. 25, 2013

(65) Prior Publication Data

US 2013/0317489 A1 Nov. 28, 2013

Related U.S. Application Data

(62) Division of application No. 12/087,434, filed as application No. PCT/FR2006/024262 on Nov. 6, 2006, now Pat. No. 8,449,587.

(30) Foreign Application Priority Data

Jan. 9, 2006 (FR) ...................................... 06 00160

(51) Int. Cl.
*A61B 19/00* (2006.01)
*A61B 18/20* (2006.01)
(Continued)

(52) U.S. Cl.
CPC ..... *A61B 18/203* (2013.01); *A61B 2018/00452* (2013.01); *A61B 2019/448* (2013.01); *A61B 2019/461* (2013.01)

(58) Field of Classification Search
CPC ........... A61B 18/20; A61B 2018/2015; A61B 2018/203; A61B 17/00491; A61B 2017/005; A61B 2017/00504; A61B 2017/00508; A61B 2017/00513; A61B 2017/00517; A61B 18/00; A61B 2018/00315; A61B 2018/00452; A61B 2018/0047; A61B 19/44; A61B 2019/448
USPC ................... 606/9–14, 214–216; 607/88–91; 128/898

See application file for complete search history.

(56) References Cited

U.S. PATENT DOCUMENTS 5,156,613 A 10/1992 Sawyer
6,032,062 A 2/2000 Nisch
(Continued)

FOREIGN PATENT DOCUMENTS

EP 1 384 446 A 1/2004
FR 2 598 088 5/1997
WO WO 97/17025 5/1997

OTHER PUBLICATIONS

International Search Report for International Application No. PCT/FR2006/002462, date of completion Mar. 28, 2007.
(Continued)

*Primary Examiner* — Ahmed Farah
(74) *Attorney, Agent, or Firm* — Mintz Levin Cohn Ferris Glovsky and Popeo, P.C.

(57) ABSTRACT

The present invention relates to a system for treatment of skin wounds, comprising an energy source for activation of a biochemical healing effect, and at least one dressing intended to be placed on the wound before the step of activation by said energy source, characterized in that said dressing comprises an identification means interacting in a contactless manner with a sensor that triggers the function of the energy source only when the distance between the sensor and said identification means is below a threshold value.

5 Claims, 1 Drawing Sheet

(51) Int. Cl.
*A61N 5/067* (2006.01)
*A61B 18/00* (2006.01)

(56) References Cited

U.S. PATENT DOCUMENTS

| | | | |
|---|---|---|---|
| 6,074,382 | A | 6/2000 | Asah et al. |
| 6,334,069 | B1 * | 12/2001 | George et al. .................... 607/2 |
| 6,773,699 | B1 * | 8/2004 | Soltz et al. ................. 424/78.03 |
| 7,307,530 | B2 | 12/2007 | Fabian et al. |
| 2002/0111609 | A1 | 8/2002 | Mordon et al. |

OTHER PUBLICATIONS

Amendment and Response to the Jan. 31, 2012 Office Action for U.S. Appl. No. 12/227,882 (10 pgs.).

Non-Final Office Action date mailed Jan. 31, 2012 for U.S. Appl. No. 12/227,882 (12 pgs.).

International Search Report for International Application No. PCT/FR2007/051321 (1 pg.).

Final Office Action dated Jan. 22, 2013 for U.S. Appl. No. 12/227,882 (14 pgs.).

Response to Jan. 22, 2013 Final Office Action dated Jun. 25, 2013 for U.S. Appl. No. 12/227,882 (12 pgs.).

Non-Final Office Action dated Jul. 19, 2013 for U.S. Appl. No. 12/227,882 (14 pgs.).

Response to Jul. 19, 2013 Action dated Dec. 20, 2013 or U.S. Appl. No. 12/227,882 (9 pgs.).

Final Office Action dated May 9, 2014 for U.S. Appl. No. 12/227,882 (14 pgs.).

Response to May 9, 2014 Final Office Action dated Oct. 9, 2014 for U.S. Appl. No. 12/227,882 ( 12 pgs.).

Advisory Action dated Oct. 21, 2014 for U.S. Appl. No. 12/227,882 (3 pgs.).

* cited by examiner

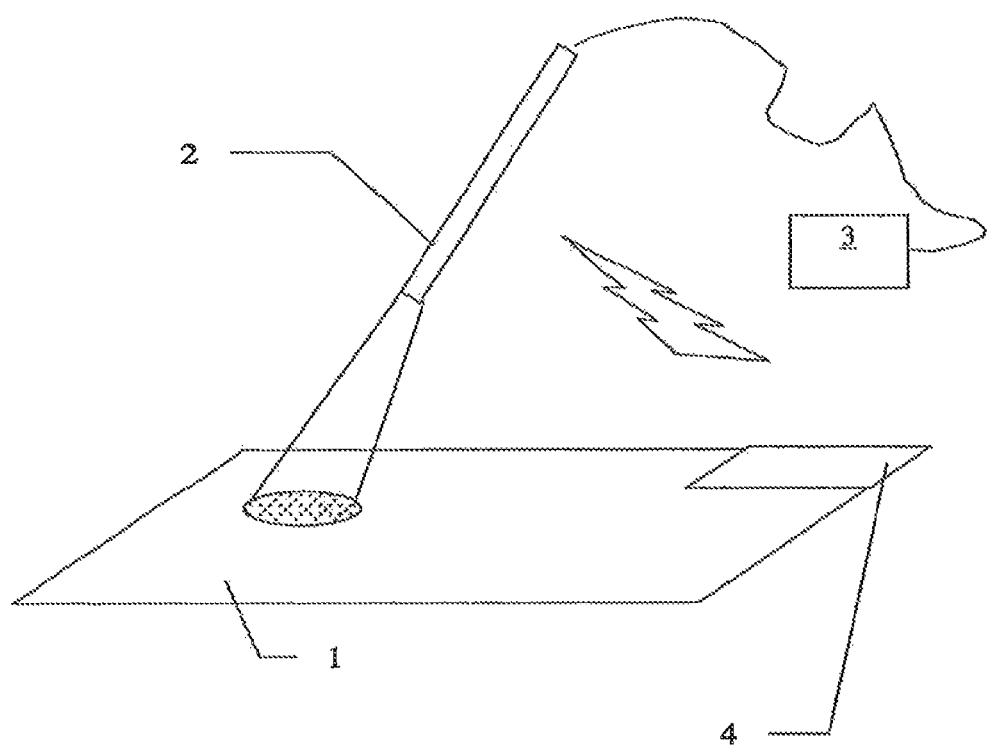

SKIN WOUND TREATMENT METHOD, DRESSING AND BIOCHEMICAL ACTIVATION DEVICE FOR THE USE OF SUCH A METHOD

CROSS-REFERENCE TO RELATED APPLICATIONS

The present application is a divisional of U.S. patent application Ser. No. 12/087,434, filed on Jul. 2, 2008, which is a 35 U.S.C. §371 national stage entry of PCT/FR2006/002462, which has an international filing date of Nov. 6, 2006, which claims the priority of France Application No. 06/00160, filed on Jan. 9, 2006, all of the disclosures of which are herein incorporated by reference in their entireties.

TECHNICAL FIELD

The present invention relates to the repair of skin wounds.

BACKGROUND

Various solutions are known in the prior art, consisting of improving the suture and healing process by using an external energy source. The lips of the wound are brought together and held in place by a dressing, which may include active ingredients that are activatable by the external energy source.

International patent application WO9717025 describes a treatment process consisting of affixing a cross-linked material containing a non-collagenous protein component onto a tissue. This cross-linked material is first placed on a target location on the tissue, and energy is then applied to the cross-linked material. The non-collagenous protein component is such that when energy is applied in an appropriate quantity, the matrix adheres to the tissue.

European patent application EP265470 describes a device for uniting the lips of a wound, comprising a laser whose emission wavelength is chosen such that it can perform tissue bonding and unite the lips of the wound, and a holding piece suitable for being secured to the tissue around the wound so as to hold the lips of said wound in contact, at least while the wound is exposed to said laser radiation. The holding piece includes at least one region suitable for being positioned over the wound and sufficiently transparent at the wavelength of laser radiation for the energy of said radiation to be sufficient, after it has passed through said region, to perform the desired tissue bonding.

Use of activation devices such as a laser source is not without danger and handling such apparatus may cause accidents if the beam is inadvertently directed towards the eye of a person present in the operating area.

SUMMARY

The aim of the present invention is to avoid such disadvantages in the prior art.

To this end, in its most general form, the invention relates to a skin wound treatment system comprising an energy source for activating a biochemical wound-healing effect and at least one dressing designed to be affixed to the wound before the activation stage is performed using said energy source, characterised in that said dressing includes an identification means that interacts without contact with a sensor that controls the operation of the energy source only when the distance between the sensor and said identification means is less than a threshold value.

Preferably, the detection distance of the identification means is below fifty centimeters.

In a preferred variant, the energy source consists of a laser source.

In a first embodiment, the identification means consists of at least one permanent magnet and is characterised in that the sensor in the device is a magnetic sensor associated with a calculator to calculate a distance according to the electromagnetic signals detected.

In a second embodiment, the identification means consists of optical markings and is characterised in that the sensor in the device is an image detector associated with a calculator to calculate a distance according to the image detected.

In a preferred embodiment, the identification means consists of a transponder.

Advantageously, the identification means includes a unique identifier for the dressing model associated with it.

Preferably, the operating settings of the energy source are controlled according to said unique identifier.

The invention also provides a dressing for use with such a system, characterised in that it includes an identification means, and additionally a biochemical activation device that includes an energy source controlled by a calculator that receives a signal from a sensor suitable for interacting with the identification means incorporated in a dressing.

The invention will best be understood by reading the following description and referring to the appended illustration, which provides a schematic view of a device as claimed by the invention.

DESCRIPTION OF DRAWINGS

FIG. 1 is a system diagram according to some embodiments of the present invention.

DETAILED DESCRIPTION

The dressing (1) is formed by a transparent film as described in European patent application EP265470. It works in cooperation with a laser source (2) controlled by a control unit (3) that supplies power to and controls the laser source.

Dressing (1) includes a radio frequency identification (RFID) tag (4). This tag includes in a known manner an induction loop providing power supply to a circuit that includes a memory in which a dressing type identifier is recorded.

This information can be used to optimise the settings of the associated energy source, in particular the power, duration and frequency of the pulses.

The handpiece (2) that includes the laser has a power supply that can activate tag (4) by means of an electromagnetic field detected by the induction loop. It also includes a sensor designed to receive electromagnetic signals emitted by RFID tag (4) when the latter is supplied with power.

Activation of the laser depends on the detection of an identification signal from a tag. If such a signal is not detected, the laser is on standby and thus prevents any risk of accident, even when inadvertently directed towards a person.

In particular, when handpiece (2) is at a distance from the dressing that is greater than the range of RFID tag (4), the laser is inactive.

The different laser control settings, according to the different types of dressing, are recorded in the memory of the laser control unit, for instance in the form of a table. These settings may be updated, particularly in the event that a new type of dressing is marketed, via a link with an external computerised device, or by data entry using an input interface incorporated in control unit (3).

The invention is not limited to an interaction between an RFID tag and a sensor.

In an equivalent variant, the interaction may take place via magnetic markers affixed to the dressing. These markers comprise thin magnet items or magnetised particles. In this case, the handpiece includes one or more magnetosensitive sensors, for instance Hall effect sensors, which output a signal according to the field amplitude detected in one or more directions. These signals are used by a calculator to determine the distance and direction of the magnetic markers affixed on the dressing, by a known method of triangulation.

In another equivalent variant, the interaction may take place by affixing an optical marking, for instance a fluorescent marking, that is excited by a secondary source fitted in the handpiece. The handpiece in this case includes an optical sensor, for instance a sensor including a CCD (charge-coupled device) associated with a calculator that analyses the image detected in order to calculate the distance and possibly the direction of the marking on the dressing from the handpiece. This marking may take the form of a matrix code or geometrical figures by which the distance may be deduced on the basis of the size and deformation of the image, as detected by the sensor in the handpiece.

The dressing may consist of a simple transparent film, by which the lips of the wounds are brought together and temporarily held in place and through which the energy provided by the handpiece can be transferred.

It may also include active coatings involved in the biochemical reactions under the effect of excitation by an energy source.

The energy source described is a laser beam. However, other equivalent energy sources such as ultrasound, radio-frequency electromagnetic waves or a thermal source may be used and would constitute a technical equivalent. Nevertheless, a laser source remains the preferred solution.

What is claimed is:

1. A dressing for use in a skin wound treatment system, the system comprising the dressing, a laser source for activating a biochemical wound-healing effect, a calculator and a sensor, wherein the laser source is at least partially controlled by the calculator, which receives a signal from the sensor, the dressing including:
    a radio frequency identification (RFID) tag having an induction loop configured to interact without contact and without electrical connection with the sensor; and
    a circuit including a memory,
        wherein:
            the dressing is configured for affixation on or adjacent a wound prior to activation of the laser source;
            the induction loop provides power to the circuit, and
            a dressing type identifier is recorded in the memory and used to control the power, duration and frequency of pulses of the laser source.

2. The dressing of claim 1, wherein the RFID tag includes a unique identifier for the dressing type associated with it.

3. The dressing of claim 1, wherein the dressing is formed of a transparent film.

4. The dressing of claim 3, wherein the edges of the wound are brought together in close proximity and temporarily held in place, and wherein the transparent film is configured to transfer energy of the laser source to an area of the wound.

5. The dressing of claim 1, wherein the dressing includes one or more coatings associated with the biochemical wound-healing effect activated by the laser source.

* * * * *